United States Patent
Golub et al.

(10) Patent No.: US 11,583,654 B1
(45) Date of Patent: Feb. 21, 2023

(54) MULTIPLE PORT AND MULTIPLE CONFIGURATIONAL MEDICAL MASK

(71) Applicants: Michael Golub, Boca Raton, FL (US); Svetlana Golub, Boca Raton, FL (US)

(72) Inventors: Michael Golub, Boca Raton, FL (US); Svetlana Golub, Boca Raton, FL (US)

(73) Assignee: MEDICAL DEVICE HOLDING COMPANY, LLC, Boca Raton, FL (US)

( * ) Notice: Subject to any disclaimer, the term of this patent is extended or adjusted under 35 U.S.C. 154(b) by 336 days.

(21) Appl. No.: 15/929,351

(22) Filed: Apr. 28, 2020

(51) Int. Cl.
 *A61M 16/00* (2006.01)
 *A61M 16/08* (2006.01)
 *A61M 16/06* (2006.01)
 *A61M 16/20* (2006.01)

(52) U.S. Cl.
 CPC ...... *A61M 16/085* (2014.02); *A61M 16/0605* (2014.02); *A61M 16/0672* (2014.02); *A61M 16/208* (2013.01); *A61M 2202/0208* (2013.01); *A61M 2202/0225* (2013.01)

(58) Field of Classification Search
 CPC ............ A61M 16/085; A61M 16/0605; A61M 16/208; A61M 2202/0208; A61M 2202/0225
 See application file for complete search history.

(56) References Cited

U.S. PATENT DOCUMENTS

| | | | | |
|---|---|---|---|---|
| 6,386,198 | B1* | 5/2002 | Rugless | A62B 23/025 128/205.25 |
| 9,498,592 | B2* | 11/2016 | Dhuper | A61M 16/20 |
| 10,426,909 | B2* | 10/2019 | Alphonse | A61M 16/0875 |
| 10,589,047 | B2* | 3/2020 | Pedro | A61G 13/121 |
| 2012/0216806 | A1* | 8/2012 | Rookard | A61M 16/06 128/203.29 |
| 2014/0243600 | A1* | 8/2014 | Eisenberger | A61M 16/1005 600/114 |
| 2014/0243698 | A1* | 8/2014 | Koch | A61B 5/6803 29/428 |
| 2017/0189635 | A1* | 7/2017 | Beard | A61M 16/0051 |

* cited by examiner

Primary Examiner — Philip R Wiest
Assistant Examiner — Sarah B Lederer
(74) Attorney, Agent, or Firm — Daniel S. Polley, P.A.

(57) ABSTRACT

A medical double configurational and multiple ports mask preferably including a multifunctional plug with or without a nebulizer oxygen delivery adaptor ("NODA") attachment. The mask fits over the mouth and the nose and preferably contains at least two possible nose/face configurational solutions. The mask can be secured over the head with a stretchable or non-stretchable material. The position of the preferred triple ports of the double configurational mask provides improved structural construction reflecting different patient's nose/face features and allows for different types of procedures to be performed at the same time regardless of the patient's head/neck position. The multifunctional plug can be used for a variety of applications. The mask can be used with existing standardized disposable respiratory care equipment, including a simplified improved nebulizer oxygen adaptor ("SINODA") and/or multifunctional use nebulizer oxygen delivery adaptor ("MUNODA") attachment.

21 Claims, 10 Drawing Sheets

MULTIPLE PORT AND MULTIPLE CONFIGURATIONAL MEDICAL MASK

1. FIELD OF DISCLOSURE

The disclosure relates generally to medical mask and particularly to a novel medical mask having multiple inlet ports preferably with universal plug.

2. BACKGROUND

General traditional masks have a single port to deliver medical gases and/or nebulized medications to a patient. The single port mask has very limited capabilities. Examples of earlier medical masks include: U.S. Pat. No. 6,386,198 B1 to Florence Rugless for a Multi-Purpose Oxygen Face Mask; U.S. Publication No. 2005/0028811 A1 to Robert Nelson et al. for a Multitask Medical Treatment Respiratory Apparatus; U.S. Publication No. 2009/0126723 A1 to Sunil Dhupar for a Patient Interface Member For Use In An Aerosol Inhalation System; U.S. Publication No. 2003/0024533 A1 to Joseph Sniadach for a Multi-Port Mask; U.S. Pat. No. 6,851,428 B2 to Camell Dennis for a Respiratory Mask; U.S. Pat. No. 4,201,205 to Victor Bartholomew for an Oxygen Mask; U.S. Pat. No. 5,353,789 to Joachin Schlobolm for a Flaccid Mask With Straps; U.S. Pat. No. 5,673,690 to Amad Tayebi for a Breathing Mask; U.S. Pat. No. 7,121,279 to Carnell Dennis for a Respiratory Mask; U.S. Des. Pat. No. D250.047 to George Lewis for a Breathing Mask; U.S. Pat. No. 4,657,010 to Stewart Wright for an Adjustable Face Mask; and U.S. Pat. No. 2,625,155 to Arthur Engelder for a Face Mask. The novel mask disclosed herein is directed to overcome and/or substantially reduce these and other problems associated with single port medical mask.

SUMMARY OF THE DISCLOSURE

Generally disclosed is a multiple port and multiple configurational medical mask which provides for increased functionality and capabilities as compared to conventional single port medical masks. The ports of the triple action mask can be preferably positioned with respect to the patient's/wearer's face at or below the lip line with a directional inward flow towards the patient's airway. The inward flow exits the multiple inlet ports and can be preferably directed and combined into a one point flow inside the mask (i.e. mixing/combining area) prior to administration of the contents flowing through the inlet ports to the patient/wearer.

The disclosed novel mask provides for a multifunctional, preferably disposable single patient use, while also providing for a double or multiple configurational mask. One non-limiting ideal user of the novel mask can be a spontaneously breathing patient. Though not considered limiting, the disclosed novel mask can be preferably discarded after each patient use. The disclosed mask can be MRI comparable, where in a preferred non-limiting embodiment it can be constructed from non-metal materials. In this regard and not considered limiting, the disclosed mask can be preferably made from a soft to semi soft translucent plastic material and secure to a patient's face with a stretchable or non-stretchable material/strap.

In a preferred embodiment, the instant disclosure provides for a novel triple port double configurational mask which can be provided with a multifunctional plug and/or traditional solid plug with or without a novel simplified improved nebulizer oxygen delivery adaptor ("SINODA") and/or multifunctional use nebulizer oxygen delivery adaptor ("MUNODA") attachment. In view of the multiple ports, preferably three ports, the disclosed novel mask is capable of being used to perform multiple tasks at the same time.

DETAILED DESCRIPTION

Figure 9:
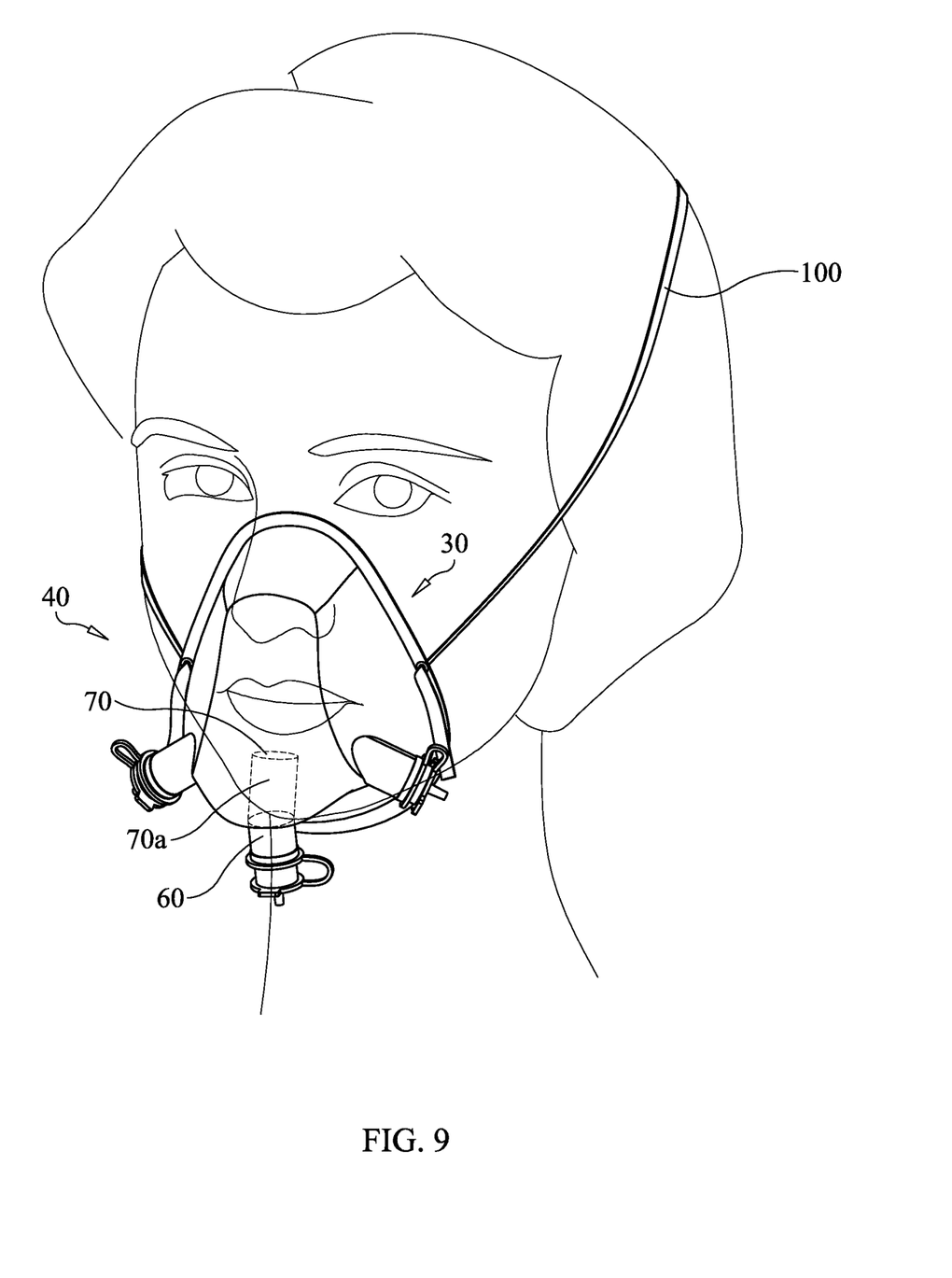
FIG. 9 is perspective view of the novel mask being worn by a patient/wearer.

As seen in FIGS. 1 through 8, a novel medical mask in accordance with the present disclosure is shown and generally designated as mask 30. Mask 30 can comprise a body member 40 having a front portion 42, a top portion 44, a first side portion 46, a second side portion 48 and a bottom portion 50. A perimeter flange 52 can be provided along the perimeter of body 40 which abuts against the wearer's face in use of mask 30 by a wearer (See FIG. 9). Preferably front portion 42, top portion 44, first side portion 46, second side portion and bottom portion 50 can be monolithically formed or constructed integral to form a one piece body 40. Body 40 has an open back area 53.

As also seen in FIGS. 1 through 8, mask 30 is preferably provided with a plurality of inlet ports, and in one non-limiting embodiment, three inlet ports 60a, 60b and 60c can be provided. Each inlet port 60 can be provided with an open inlet end 62 and terminates at a second end with a corresponding opening 70 in body 40 to form an open second or outlet end. The outlet ends of ports 60/openings 70 terminate into the same single mixing area 80 defined by the body member 40. Each inlet port 60 can be preferably independent and isolated from the other or remaining inlet ports. Thus, in the preferred embodiment, the content traveling through passageways 66 of the inlet ports 60 are separated from each other until they preferably leave the inlet ports (i.e. out of the second end of port 60/opening 70) and enter into mixing area 80 where they can be mixed or combined together (i.e. depending on the nature of the various content(s)) for administration or delivery to the patient/wearer. Thus, all ports 60 preferably provide for a directional flow of the content traveling within the ports with all content directed into one flow point (mixing area 80) within mask 30.

Inlet ports 60 can be secured or positioned with respect to body 40 at angle to further direct and assist with the flow of the content through internal passageway into mixing area 80. Preferably, opening 70/second end of ports 60 is positioned at or below the lip/lips line (See FIG. 9) at an angle to assist in a directional inward flow towards the patient's airway.

Preferably, inlet ports 60 are monolithically formed or constructed integral with body 40 to provide for a one-piece multiple ports medical mask 30.

Figure 1:
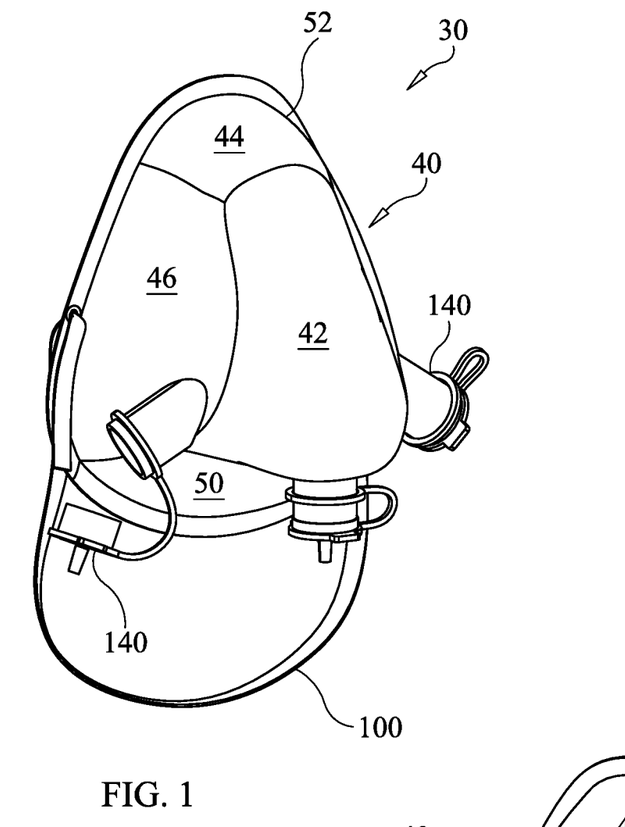
FIG. 1 is a front perspective view of the novel mask, with port caps, plugs or covers attached, in accordance with the present disclosure.
Figure 2:
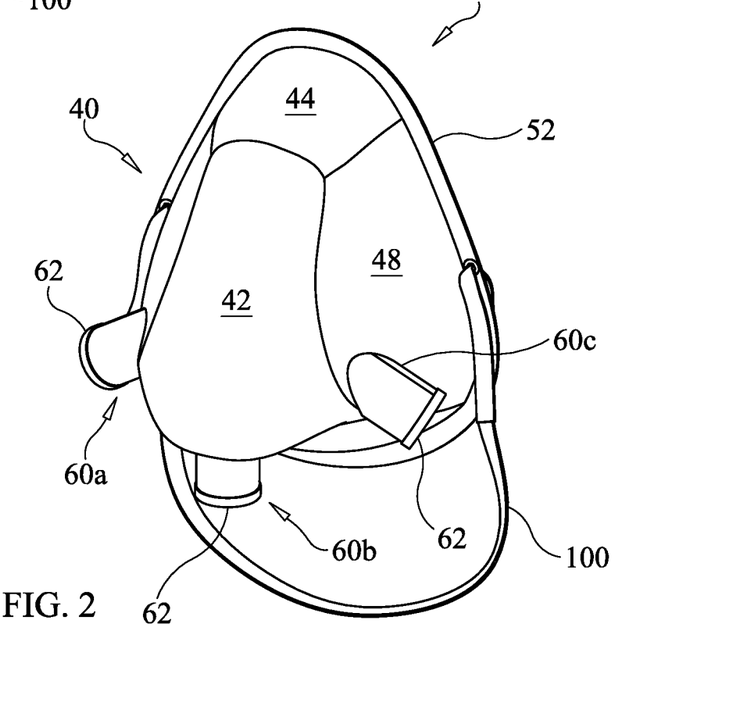
FIG. 2 is another front perspective view of the novel mask of FIG. 1.
Figure 3:
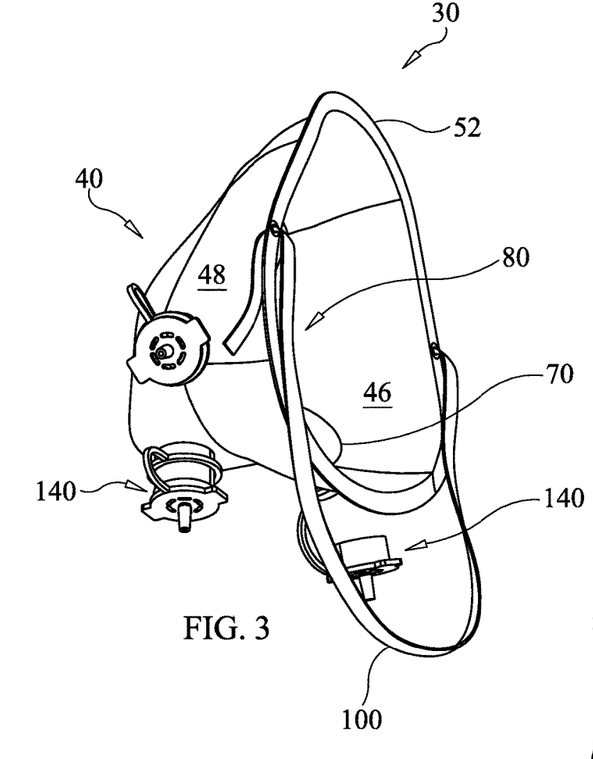
FIG. 3 is back side perspective view of the novel mask of FIG. 1.
Figure 4:
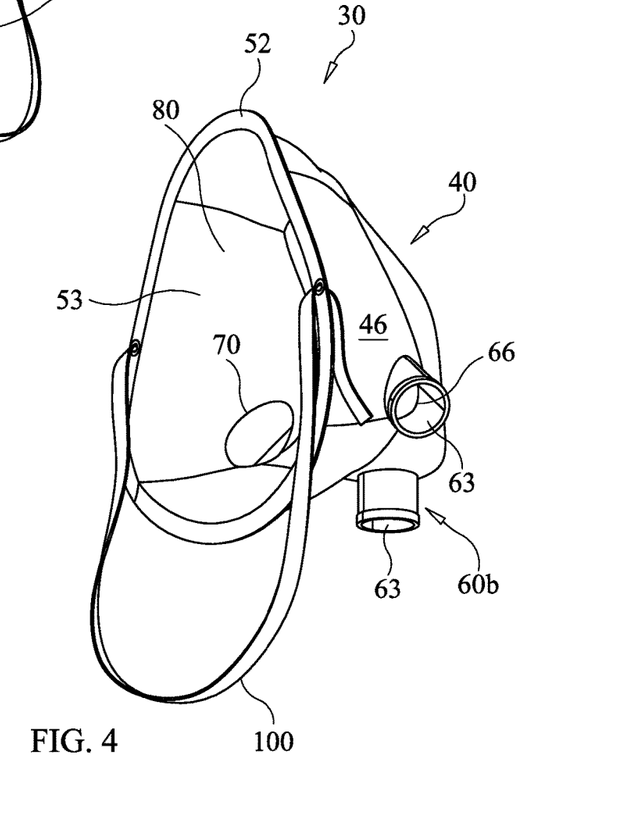
FIG. 4 is another back side perspective view of the novel mask of FIG. 1.
Figures 5, 6:
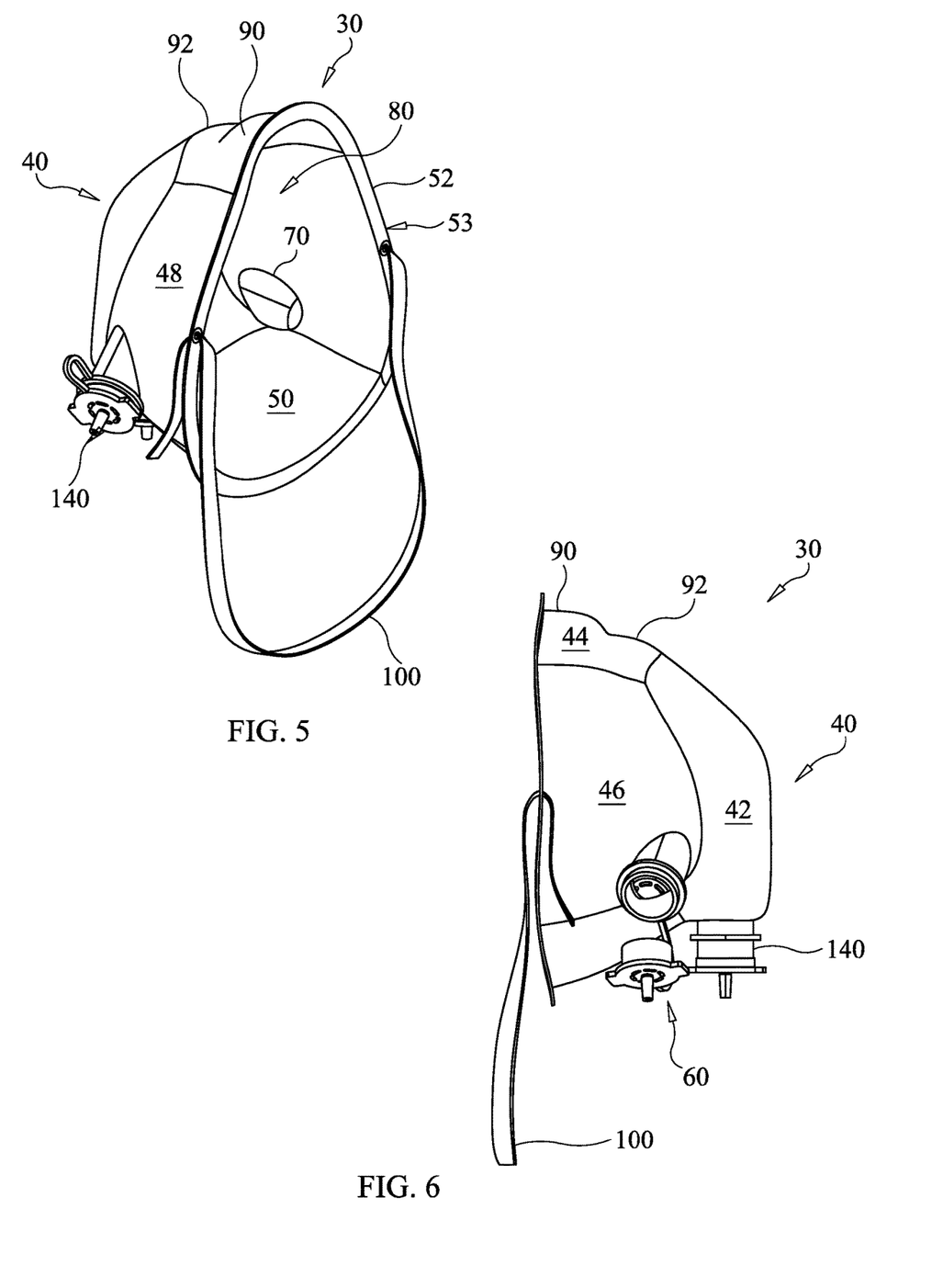
FIG. 5 is a further back side perspective view of the novel mask of FIG. 1.
FIG. 6 is a side elevational view of the novel mask of FIG. 1.
Figure 7:
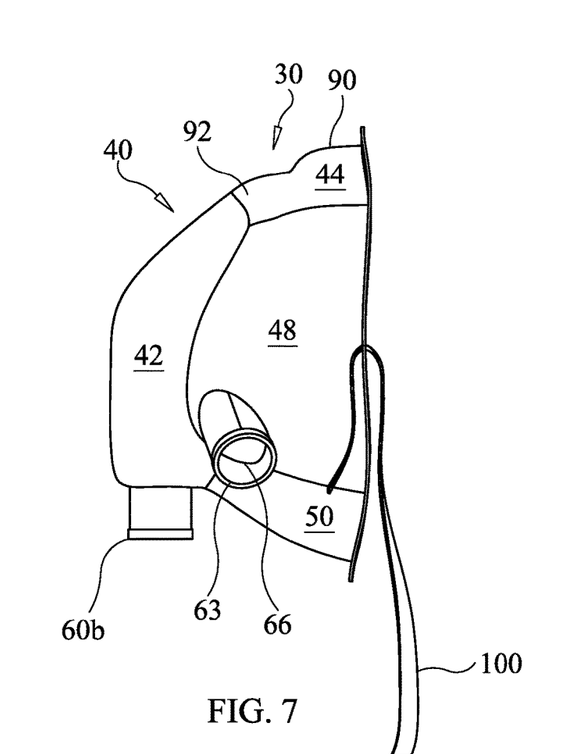
FIG. 7 is another side elevational view of the novel mask of FIG. 1.
Figure 8:
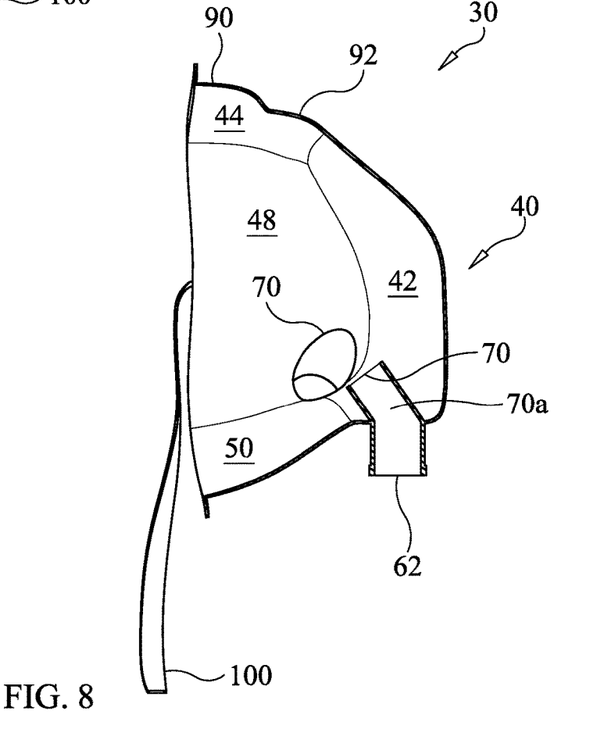
FIG. 8 is a side sectional view of the novel mask of FIG. 1.

As best seen in FIG. 6, in a preferred embodiment mask 30 can be a double configurational mask which can preferably have two available possible nose/face applications 90 and 92 based on the person's/wearer's nose/face features (pediatric/juvenile to adults). With the preferred double configurational application of the mask 90 or 92, an improved seal is promoted and achieved between the mask along perimeter flange 52 and the patient's face in use.

Medical mask 30 can be secured to the patient's/wearer's head by any conventional mechanism. In a preferred embodiment, a stretchable or non-stretchable material, such as, without limitation, a band/cord/strap 100 can be used (as a non-limiting example see FIG. 9). However, other non-limiting securement techniques such as, without limitation, two cords, straps, laces, etc. that are tied together at the back of the patient's head can also be used and are considered within the scope of the disclosure.

FIGS. 10-15 illustrate a port cap, plug or cover 140 (collectively "cover"), which can be a piece of material serving to fill the hole/opening 63 of the first outer end 62 of inlet port 60. Each cover 140 can be used for a particular inlet port 60 and thus, in the preferred embodiment having three inlet ports, preferably three covers 140 can be provide, though such is not considered limiting. Each cover 140 can be provided with an outer member 142 having an inside surface 144 and an outside surface 146. A protrusion or cylinder 148 (collectively "cylinder 148") can extend upward/outward from inside surface 144 and can be inserted within opening 63 of associated inlet port 60 when cover 140 is in use. In a preferred embodiment the material selected for constructing cover 140 can be stronger/tougher compared to the material selected for constructing main body 40 of mask 30.

Preferably, at least one of the covers 140 can be provided with a connector or tip 150 (collectively "connector 150") extending downward/outward from outside surface 146 for connecting an air and/or oxygen tubing to cover 140. Preferably, connector 150 can be centrally located though it is also within the scope of the disclosure for connector 150 to be positioned off center. Connector 150 can include a passageway 152 extending from a first outer end 154 to a second inner end 156 which provides the conduit/path for air/gas received from the attached tubing to travel into the inlet port 60 that the cover 140 with connector 150 is secured to. Also, preferred, though not limiting, is that the cover 140 material also be from a non-metal material to allow the covers 140 to be secured to body 40 during a MRI procedure.

Figure 10:
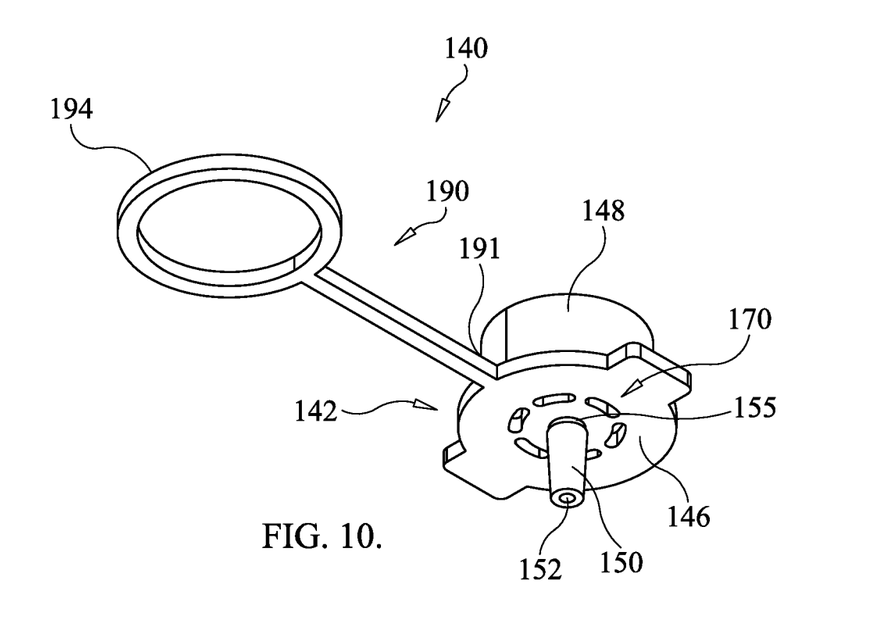
FIG. 10 is a perspective view of a novel port cap/plug/cover in accordance with the present disclosure.
Figure 15:
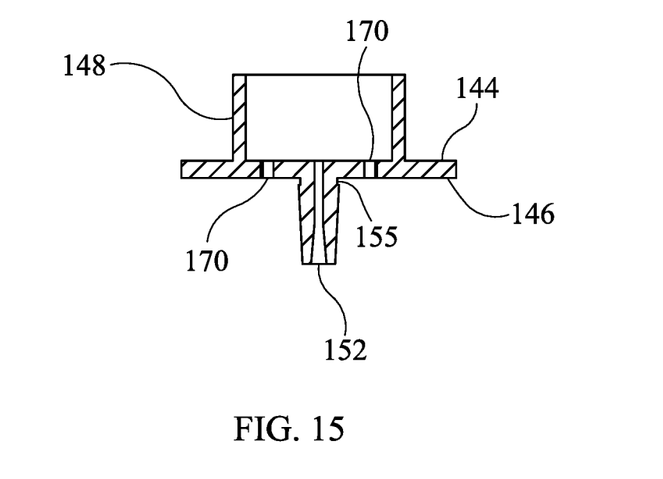
FIG. 15 is a sectional view of a portion of the cap/cover of FIG. 10 illustrating the internal openings.

In use, cover 140 can be used to partially or fully close a particularly inlet 60 to which cylinder portion 148 it is inserted within, depending on whether cover 140 is or is not provided with connector 150 and/or one or more escape apertures/holes/slots/openings 170 (collectively "apertures 170" which will be discussed in further detail below.

Figure 11:
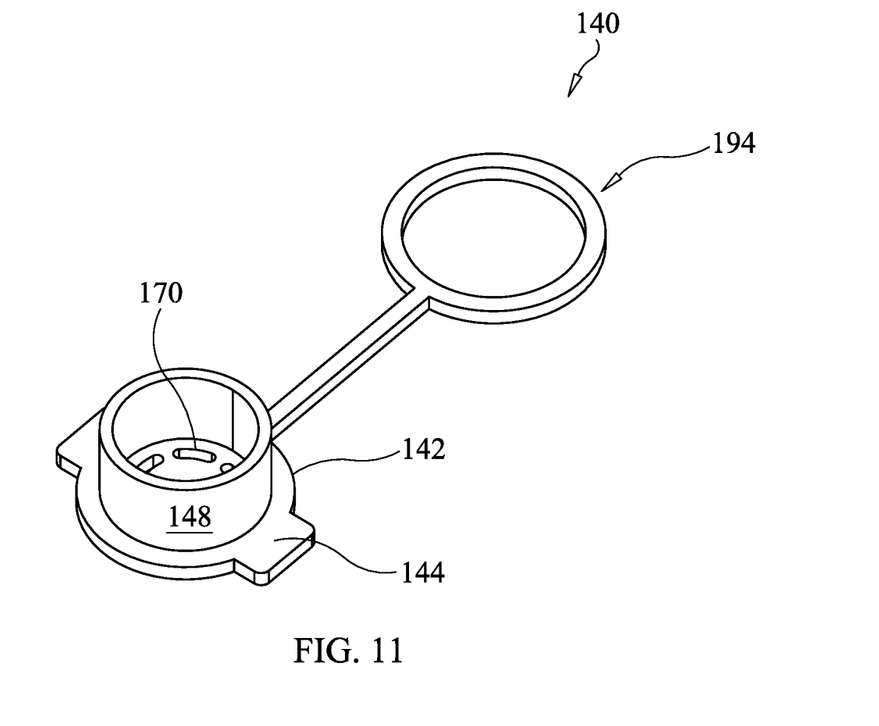
FIG. 11 is another perspective view of the port cap/cover of FIG. 10.

To help reduce loss of covers 140 and to have such covers 140 readily available for use, a cord, lanyard, etc. (collectively "cord 190") can be provided and can be attached or monolithically formed/constructed integral at one end 191 with cover 140 and can be provided with a loop member 194 at its opposite end. Associated inlet 60 can be snugly/tightly inserted/received through loop member 194 to allow cover 140 to be secured to its associated inlet 60, preferably at all times (i.e. whether or not cover 140 is in use to partially or fully closed associated inlet 60). Thus, preferably cover 140 can be designed to be secured to inlet 60 by disposing loop member 194 over the associated inlet port 60, in order to also achieve preferably interchangeability and transferable capabilities.

A groove 155 can be provided at the base of connector 150 for holding a ring, washer, band, etc. 180 (collectively "washer 180") in place. Connector 150 can slightly taper outward in outer diameter until it reaches groove 155 to assist in maintaining an air/oxygen/gas tubing thereto. Opening 182 in washer 180 can be sized to tightly receive connector 150 and to allow washer 180 to received and rests within groove 155. Once in groove 155, washer 180 will remain secured in position at the base of connector 150 adjacent/abutting outside surface 146. Preferably, a plurality of apertures 170 can be provided through outer member 142 of cover 140. Though preferably being centrally located and forming a circular pattern, apertures can be provided anywhere on outer member 142 and do not have to form a circular pattern nor be centrally located. Apertures 170 are provided to allow carbon dioxide from patient exhalation to escape out of body 40 of mask 30 and thus eliminating, reducing and/or reducing an amount of carbon dioxide that the patient may inhale during inhalation. Upon exhalation, enough breath force is exerted through apertures 170 to move washer 180 from abutting apertures 170 (while not enough force to remove washer 180 out of groove 155 and, thus, washer 180 remains secured at the base of connector 150). The movement of washer 180 away from apertures 170 allows the exhaled carbon dioxide to escape through apertures 170 into the atmosphere. Accordingly, washer 180 acts like or similar to a one-way valve for cover 140 to cover apertures 170 for medical gas retention during inhalation and carbon dioxide elimination during exhalation.

Figure 12:
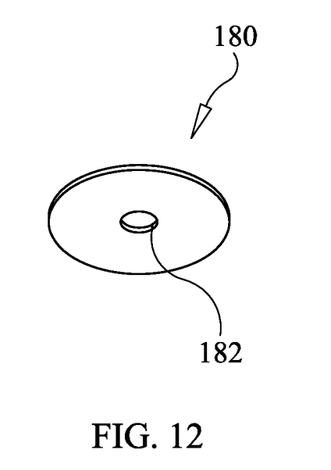
FIG. 12 is a perspective view of a washer/ring that can be used with the port cap/cover of FIG. 10.
Figure 13:
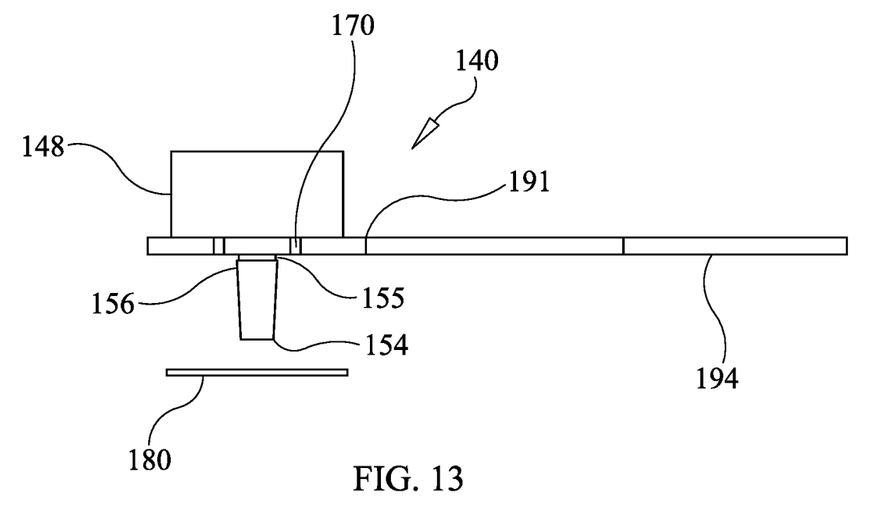
FIG. 13 is an exploded side elevational view of the port cap/cover of FIG. 10.
Figure 14:
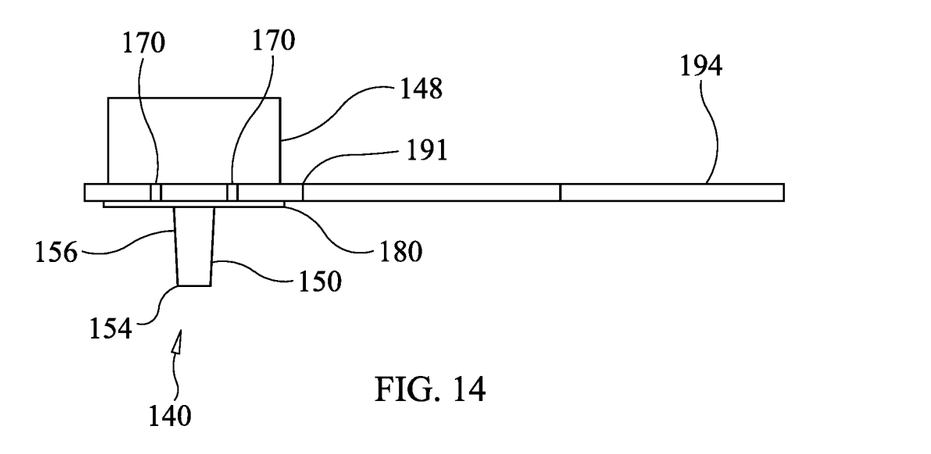
FIG. 14 is a side elevational view of the port cap/cover of FIG. 10.

Likewise, during inhalation (and when a sufficient exhalation breath force is not occurring) washer 180 remains abutted against outside surface 146 of outer member 142 which covers apertures 170. Thus, during inhalation or when gas is introduced through an inlet port 60 and into single point area 80 (i.e. through tubing attached to connector 150), the gas is prevented from escaping through apertures 170 by abutting washer 180 and is available for inhalation by the patient. Accordingly, preferably rubber or silicone washer 180 can be designed to be placed over apertures 170 of cover 140 in order to preserve medical gas inside mask body 40 during the inhalation process.

The position/location of openings 70 in main body 40 in relationship to the wearer's mouth, and, when cover 140 is secured to the associated inlet 60, aperture(s) 170 in cover 140, allow by gravity the drainage of body fluids out of mask 30 and thus provides a safety feature by preventing or reducing the chance of the patient swallowing the body fluids.

Cover 140 can be adapted to utilize existing disposable respiratory care technology, devices and/or accessories. Cover 140 can be configured and/or designed to receive a metered dose inhaler ("MDI").

Some non-limiting examples concerning the uses for one or more of inlets/inlet ports 60 can include:

1. One or more ports 60 being provided with a piece of corrugated tubing to serve as a reservoir during heliox therapy. As a heliox gas mixture is lighter than oxygen, the above noted-angled downward and lip line or below position of the ports 60 with respect to mask body 40 assists in capturing and/or preserving more of the heliox mixture for use by the patient and reduces the amount of the mixture that evaporates into the atmosphere.

2. All three ports 60 can be adapted and/or configured to receive high or low oxygen/helium concentration, nitric oxide, as well as air.

3. Ports 60 can be adapted and/or configured to cold or heated humidified air or oxygen through connected of the gas source outlet to one or more of the ports 60.

4. All three positions of ports 60 (where three ports are provided) coexist for use and can be used simultaneously for inserting and maintaining surgical instruments, catheters, Yankaeur suction tips and other suctioning and oral suctioning tools/devices, tubes, suction catheters, other medical devices etc.

5. All three positions of ports 60 can allow for several tasks concerning or related to the patient/wearer of mask 30 to be performed or accomplished simultaneously. Thus, each port 60 can be used at the same time with the other ports 60 of mask 30.

6. The position of openings 70 allow for the placement of NO (nasogastric) and/or OG (orogastric) tubes right thru it, which can eliminate or reduce the necessity of placing mask 30 over such tubes. Thus, mask to face sealing problems are eliminated or reduced, which can result in the elimination or reduction of skin breakdown or pressure sores. 27. The improved seal between the patient's face and mask 30 helps to enforce a closed system concept application.

7. The angular position of ports 60 provide for triple gravity (i.e. preferred three port 60a, 60b and 60c embodiment) based on direct flow openings which can allow for the maintenance of proper patient oxygen saturation while simultaneously performing medical procedures (i.e. coexisting). However it is also within the scope of the disclosure that one or more of the inlets 60 can be positioned parallel or perpendicular with respect to the body 40.

The preferred double configurational mask 30 can use or incorporate or be secured with various nebulizer oxygen delivery adaptor attachments, including adaptor attachments discloses in our U.S. Pat. No. 10,441,739 issued on Oct. 15, 2019 as well as modified or simplified versions of such attachments, including the previously mentioned MUNODA/SINODA. Providing one or more plugs for at least some of the ports 60, mask 30 along with a modified or simplified adaptor attachment from those disclosed in our U.S. Pat. No. 10,441,739 patent can be provided as part of a universal respiratory kit.

Mask 30 can be preferably constructed from soft to semi soft plastic (preferably clear or semi clear) materials, though such is not considered limiting and other materials can also be used for the construction of mask 30. Preferably, mask 30 is not constructed from nor uses any metal material in order for the mask to be MRI compatible.

Though not considered limiting, a preferred material for plug/cap/cover 140 can be a semi-soft to harder plastic material., a preferred material for body 40 can be a soft to semi-soft plastic material and a preferred material for flexible ring/washer 180 can be a soft, light, flexible material, such as, but not limited to, silicone or rubber.

In use, given the position and angular orientation of ports 60, and in some instances the varying configurations that certain of the medical devices can be secured to ports 60, slight tilting of the patient's head from side to side typically should not stop aerosolized medication delivery and/or medical gases, procedures, view of angle varieties of the contraction.

Accordingly, the disclosure provides for a novel medical mask 30 having multiple inlets 60 that all outlet into a single point (i.e. mixing area 80) prior to delivery or administration to the patient. The outlets 70 are disposed at the lip line or below and the inlets 60 oriented at a downward angle with respect to mask body 40. Though not limiting, mask 30 can be for single patient use and thus can be disposable and discarded after use. Various existing medical devices and accessories can be secured to the inlet ports 60 of medical mask 30, and mask 30 preferably provides for a closed system concept.

In one non-limiting application for mask 30, medical gases (e.g. air, oxygen, heliox mixture, nitric oxide, etc.) and a nebulized medicine can be simultaneously delivered to the patient at various rates and concentrations.

Major types of accessories that can be used in conjunction with mask 30 include, without limitation, many of the accessories employed in the delivery of gas therapy. Non-limiting examples of specific products include simple aerosol delivery systems, Venturi oxygen delivery systems, as well most forms of high or low adult, pediatric and neo-natal aerosol delivery systems. Additionally, it is also within the scope of the disclosure to provide mask 30 along with one or more other medical parts/components/equipment as a respiratory kit or complete respiratory kit. As further non-limiting examples, mask 30 can be provided in a combination with one or more of the following respiratory components: a nebulization cup, a simple oxygen mask adapter, a flappy rubber valve, corrugated tubing, a Venturi device, a reservoir bag, etc. Additional non-limiting devices/accessories that can be used with mask 30 can include: nebulizers, dual or triple nebulizers, nebulization cups, respiratory equipment, gas or oxygen reservoir bags, cool aerosol devices, tubing, corrugated tubing, oxygen hoses, medical hoses, nebulized medicine hoses, etc.

Mask 30 can be used with existing respiratory medications. At the same time mask 30 can also deliver and/or mix different medical gases, such as, but not limited to, air, oxygen, nitric oxide and/or a heliox mixture.

Mask 30 and/or body 40 can be considered fixed or fixed structure (i.e. preferably not containing adjustable pieces, such as, without limitation, adjustable accordion folds, etc.) one-piece medical mask. In use of mask 30 can provide for the elimination or at least reduction of facial skin breakdown, as compared to other harder material mask, in view of the material (i.e. soft material) selected for body 40 and in view of the structure of mask 30 (i.e. NG and/or OG tubes can be placed, secured and maintained right through the mask's openings—thus also allowing for a better seal of body 40 to the patient's face.).

A provided tube connector can have the ability to receive and deliver a metered dose inhaler (MDI). The tube connector or connector can be adapted for receiving and utilizing the MDI preferably through means of an internal passageway within the connector. This provides for additional multi-functionality and multi-tasking of the plug and mask 30.

Preferably, the middle port/inlet 60 can be parallel (vertical) with mask body 40, as compared to the preferred angled nature of the side inlets 60. Though preferably parallel from an external view and internal portion terminating at middle opening 70 inside mask body 40 that is in communication with the middle inlet 60 can be preferably angled to direct the content out of middle opening 70 towards the patient airway.

Figure 16:
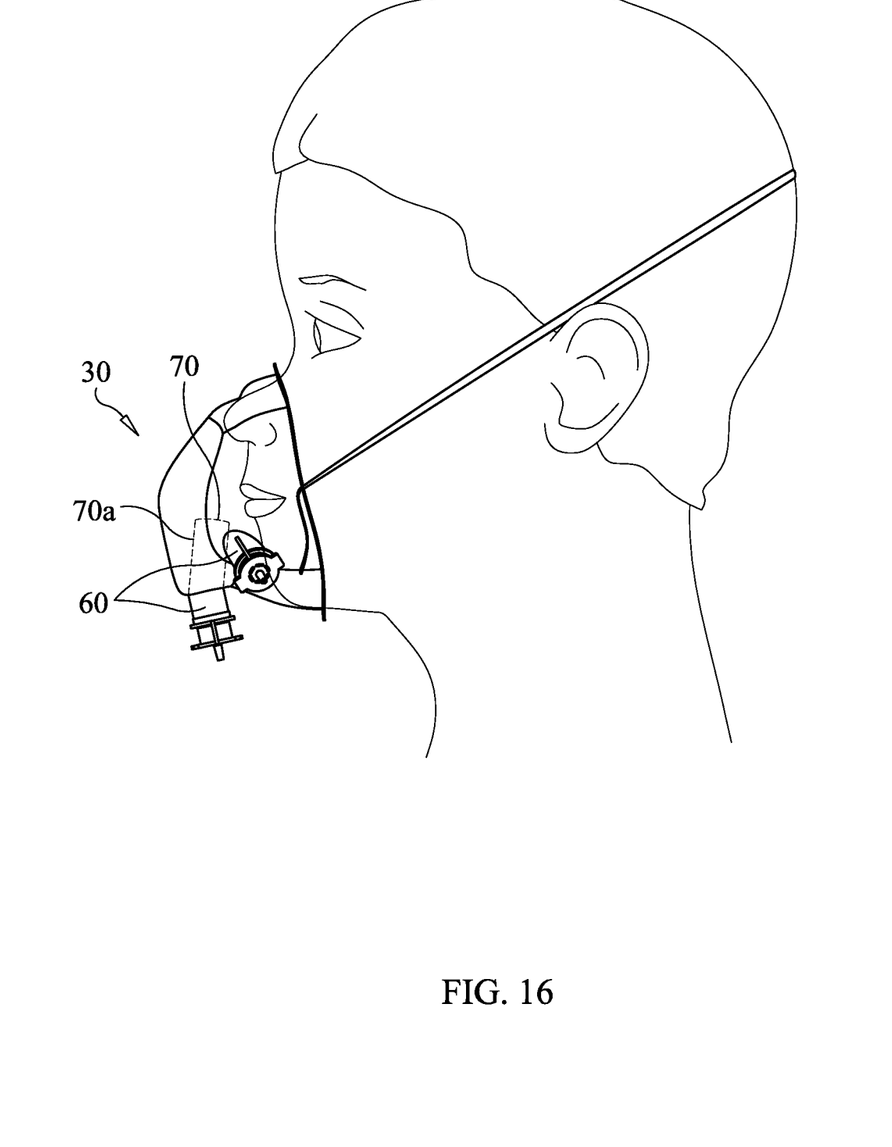
FIG. 16 is a side view of the novel mask being worn by a patient/wearer showing a first non-limiting configuration.
Figure 17:
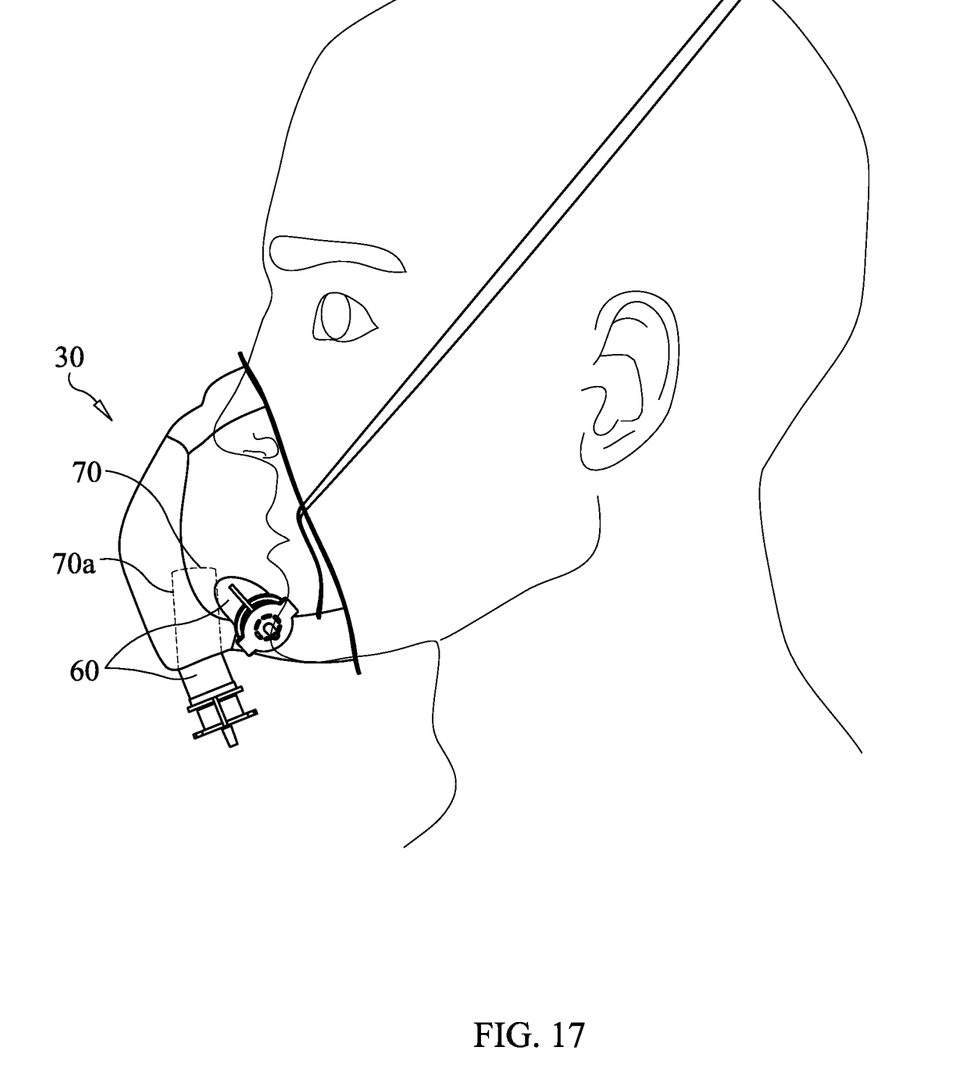
FIG. 17 is a side view of the novel mask being worn by a patient/wearer showing a second non-limiting configuration.

Preferably, mask 30 is disposed over a patient's chin area in use and can have at least two positions with respect to the nose area of the patient's face. A first non-limiting mask 30 position can position mask 30 way up on the patient's nose with a little chin covering (FIG. 16) and a second non-limiting mask 30 position can position mask 30 closer to the end of the patient's nose with a deeper chin covering (FIG. 17). The multiple positions of mask 30, allows mask 30 to be considered a multi configurational medical mask. As also seen in FIGS. 16 and 17, mask 30 can have different points of contact with respect to the patient's nose, and can also be dependent on whether the mask is being worn by a juvenile/child (i.e. pediatric) (FIG. 16) or by an adult (FIG. 17).

All components of the present disclosure mask and their attachment locations, materials, sizes, shapes, attachment mechanisms, types of inlet gases and content, types of objects (e.g. hoses, tubes, etc.) secured to the receiving inlet ports, etc. discussed above or shown in the drawings, if any, are merely by way of example and are not considered limiting and other component(s) and their attachment locations, materials, sizes, shapes, attachment mechanisms, types of inlet gases and content, types of objects (e.g. hoses, tubes, etc.) secured to the receiving inlet ports, etc. currently known and/or later developed can also be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed, whether during prosecution of this application or in litigation or similar proceeding. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related or could be attributed to the function of the "means for" language.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A multiple inlet medical mask, comprising:
   a body shaped and sized to be disposed over a mouth area and at least a lower portion of a nose area of a wearer in use, the body having a plurality of openings disposed along a side or front area of the body, each of the plurality of openings are configured to be disposed at or below a lip line level of the wearer when the body is secured to a face area of the wearer,
   the body defining a single point administrating area and having an open back to define a back edge, the body having a solid no-apertures/no-passageways upper portion beginning just above a highest opening of the plurality of openings and configured to be disposed and begin at or just below the lip line level and with the upper portion extending to a top end of the body, the upper portion comprising a majority of a vertical length of the body from a bottom end of the body to the top end of the body; wherein in use the no-apertures/no-passageways upper portion of the body captures and retains rising gases within the mask for inhalation by the wearer, and
   a plurality of elongated inlets having a first end and a second end, each elongated inlet having an internal passageway extending from the first end to the second end, each of the plurality of elongated inlets having its second end permanently positioned at a corresponding one of the plurality of openings to provide communication between the single point administrating area and the internal passageway of each elongated inlet.

2. The medical mask of claim 1 wherein each of the plurality of elongated inlets extending downward from a corresponding opening of the plurality of openings to allow for a directional inward flow of content through the internal passageway of each inlet towards an airway of the wearer when the body is secured to the wearer's face; wherein a first side inlet and a second side inlet of the plurality of inlets also taper outward at an angle from their corresponding specific openings of the plurality of openings.

3. The medical mask of claim 1 wherein the body having a top portion, the top portion having at least two permanently shaped nose receiving cavities to allow the body to be properly secured to the wearer by resting a nose bridge of the wearer into one of the permanently shaped nose receiving cavities, wherein each nose receiving cavity independent from all other nose receiving cavities and are adjacent to each other.

4. The medical mask of claim 1 wherein the body having an outer perimeter flange extending along and outward from the back edge of the body, wherein in use the perimeter flange resting along the wearer's face to create a seal between the wearer's face and the body.

5. The medical mask of claim 1 wherein the body and the plurality of elongated inlets are monolithically formed or constructed integral to provide for a one-piece medical mask.

6. The medical mask of claim 1 further comprising a cover for fully or partially closing an associated inlet from the plurality of inlets at the first outer end of the associated inlet, the cover having an outer member having an inside surface and an outside surface and an inner member extending upward from the inside surface of the of the outer member.

7. The medical mask of claim 6; wherein the inner member is shaped corresponding to the shape of the inlet.

8. The medical mask of claim 7 wherein the inner member is an cylinder, wherein in use of the cover the cylinder is received within the internal passageway of an associated inlet at the first outer end of the associated inlet such that the outer member of the cover abuts against an outer edge of the first end of the associated inlet.

9. A multiple inlet medical mask, comprising:
a body shaped and sized to be disposed over a mouth area and at least a lower portion of a nose area of a wearer in use, the body having a plurality of openings disposed along a side or front area of the body, each of the plurality of openings are configured to be disposed at or below a lip line level of the wearer when the body is secured to a face area of the wearer, the body defining a single point administrating area and having an open back to define a back edge; and
a plurality of elongated inlets having a first end and a second end, each elongated inlet having an internal passageway extending from the first end to the second end, each of the plurality of elongated inlets having its second end permanently positioned at a corresponding one of the plurality of openings to provide communication between the single point administrating area and the internal passageway of each elongated inlet;
a cover for fully or partially closing an associated inlet from the plurality of inlets at the first outer end of the associated inlet, the cover having an outer member having an inside surface and an outside surface;
wherein the outer member having at least one aperture extending therethrough from the inside surface to the outside surface and a connector extending outward from the outside surface of the outer member, the connector having an internal passageway extending therethrough which is in communication with the internal passageway of the associated inlet when the cover is in use secured to the associated inlet.

10. The medical mask of claim 9 further comprising a washer secured at a base area of the connector, the connector adapted for securement of a medical gas tubing and when the tubing is secured the internal passageway of the associated inlet is in communication with tubing through the internal passageway of the connector to receive medical gas being delivered through the tubing to the wearer; wherein in use during non-wearer exhalation and non-wearer fluid drainage periods the cover is disposed over the at least one aperture to help prevent or reduce escape of the medical gas through the at least one aperture.

11. The medical mask of claim 10 wherein during exhalation by the wearer a force of an exhalation breath of the wearer causes to washer to move away with respect to the at least one aperture to allow carbon dioxide from the exhalation breath to escape out through the at least one aperture so not to be breathed in by the wearer during inhalation.

12. The medical mask of claim 1 wherein the plurality of elongated inlets are three elongated inlets and the body having three openings, each elongated inlet of the three elongated inlets associated with a specific one of the three openings, wherein a middle elongated inlet of the three elongated inlets positioned lower on the body as compared to a position of a first left side elongated inlet and a second right side elongated inlet of the three elongated inlets on the body.

13. A multiple inlet medical mask, comprising:
a body shaped and sized to be disposed over a mouth area and at least a lower portion of a nose area of a wearer in use, the body having a plurality of openings disposed along a side or front area of the body, each of the plurality of openings are configured to be disposed at or below a lip line level of the wearer when the body is secured to a face area of the wearer, the body defining a single point administrating area and having an open back to define a back edge, the body having a top portion, the top portion having at least two permanently shaped nose receiving cavities to allow the body to be properly secured to the wearer by resting a nose bridge of the wearer into one of the permanently shaped nose receiving cavities, each nose receiving cavity independent from all other nose receiving cavities and are adjacent to each other; and
a plurality of elongated inlets having a first end and a second end, each elongated inlet having an internal passageway extending from the first end to the second end, each of the plurality of elongated inlets having its second end permanently positioned at a corresponding one of the plurality of openings to provide communication between the single point administrating area and the internal passageway of each elongated inlet; each of the plurality of elongated inlets extending downward from a corresponding opening of the plurality of openings to allow for a directional inward flow of content through the internal passageway of each inlet towards an airway of the wearer when the body is secured to the wearers face;
wherein the body and the plurality of elongated inlets are monolithically formed or constructed integral to provide for a one-piece medical mask.

14. The medical mask of claim 13 wherein the body having an outer perimeter flange extending along and outward from the back edge of the body, wherein in use the perimeter flange resting along the wearer's face to create a seal between the wearer's face and the body; wherein the body having a solid no-apertures/no-passageways upper portion beginning just above a highest opening of the plurality of openings and configured to be disposed and begin at or just below the lip line level and with the upper portion extending to a top end of the body, the upper portion comprising a majority of a vertical length of the body from a bottom end of the body to the top end of the body; wherein in use the no-apertures/no-passageways upper portion of the body captures and retains rising gases within the mask for inhalation by the wearer; wherein a middle elongated inlet of the three elongated inlets positioned lower on the body as compared to a position of a first left side elongated inlet and a second right side elongated inlet of the three elongated inlets on the body; wherein the first left side elongated inlet and the second right side elongated inlet taper outward at an angle from their corresponding opening of the plurality of openings.

15. The medical mask of claim 13 further comprising a cover for fully or partially closing an associated inlet from the plurality of inlets at the first outer end of the associated inlet, the cover having an outer member having an inside surface and an outside surface and an inner cylinder member extending upward from the inside surface of the of the outer member; wherein in use of the cover the inner cylinder member is received within the internal passageway of the associated inlet at the first outer end of the associated inlet such that the outer member of the cover abuts against an outer edge of the first end of the associated inlet.

16. The medical mask of claim 15 wherein the outer member having at least one aperture extending therethrough from the inside surface to the outside surface and a connector extending outward from the outside surface of the outer member, the connector having an internal passageway extending therethrough which is in communication with the internal passageway of the associated inlet when the cover is in use secured to the associated inlet.

17. The medical mask of claim 16 further comprising a washer secured at a base area of the connector, the connector adapted for securement of a medical gas tubing and when the tubing is secured the internal passageway of the associated inlet is in communication with the tubing through the internal passageway of the connector to receive medical gas or medicine being delivered through the tubing to the wearer; wherein in use during non-wearer exhalation and non-wearer fluid drainage periods the cover is disposed over the at least one aperture to help prevent or reduce escape of the medical gas through the at least one aperture; wherein during exhalation by the wearer a force of an exhalation breath of the wearer causes to washer to move away with respect to the at least one aperture to allow carbon dioxide from the exhalation breath to escape out through the at least one aperture so not to be breathed in by the wearer during inhalation.

18. A multiple inlet medical mask, comprising:
a body shaped and sized to be disposed over a mouth area and at least a lower portion of a nose area of a wearer in use, the body having three openings disposed along a side or front area of the body, each of the three openings are configured to be disposed at or below a lip line level of the wearer when the body is secured to a face area of the wearer with a middle front opening of the three openings positioned lower on the body as compared to the other two openings of the three openings, the body defining a single point administrating area and having an open back to define a back edge, the body having a top portion, the top portion having at least two nose receiving cavities to allow the body to be properly secured to a larger number of wearers; and
three elongated inlets, each elongated inlet having a first end and a second end, each elongated inlet having an internal passageway extending from the first end to the second end, each of the three inlets having its second end permanently positioned at a corresponding specific one of the three openings to provide communication between the single point administrating area and the internal passageway of each elongated inlet; each of the three elongated inlets extending downward from its corresponding specific opening of the plurality of openings to allow for a directional inward flow of content through the internal passageway of each inlet towards an airway of the wearer when the body is secured to the wearer's face;
wherein a first side inlet and a second side inlet of the three elongated inlets also taper outward at an angle from their corresponding specific openings of the three openings;
wherein the body and the three elongated inlets are monolithically formed or constructed integral to provide for a one-piece fixed structure medical mask.

19. The medical mask of claim 18 wherein the body having an outer perimeter flange extending along and outward from the back edge of the body, wherein in use the perimeter flange resting along the wearer's face to create a seal between the wearer's face and the body; wherein the body having a solid no-apertures/no-passageways upper portion beginning just above a highest opening of the plurality of openings and configured to be disposed and begin at or just below the lip line level and with the upper portion extending to a top end of the body, the upper portion comprising a majority of a vertical length of the body from a bottom end of the body to the top end of the body; wherein in use the no-apertures/no-passageways upper portion of the body captures and retains rising gases within the mask for inhalation by the wearer; wherein the body having a top portion, the top portion having at least two permanently shaped nose receiving cavities to allow the body to be properly secured to the wearer by resting a nose bridge of the wearer into one of the permanently shaped nose receiving cavities, each nose receiving cavity independent from all other nose receiving cavities and are adjacent to each other.

20. The medical mask of claim 18 further comprising a cover for fully or partially closing an associated inlet of the three inlets at the first outer end of the associated inlet, the cover having an outer member having an inside surface and an outside surface and an inner cylinder member extending upward from the inside surface of the of the outer member; wherein in use of the cover the inner cylinder member is received within the internal passageway of the associated inlet at the first outer end of the associated inlet such that the outer member of the cover abuts against an outer edge of the first end of the associated inlet; wherein the outer member having a plurality of apertures extending therethrough from the inside surface to the outside surface and a centrally disposed connector extending outward from the outside surface of the outer member, the connector having an internal passageway extending therethrough which is in communication with the internal passageway of the associated inlet when the cover is in use secured to the associated inlet; and
a washer secured at a base area of the connector, the connector adapted for securement of a medical gas tubing and when the tubing is secured the internal passageway of the associated inlet is in communication with the tubing through the internal passageway of the connector to receive medical gas being delivered through the tubing to the wearer;
wherein in use during non-wearer exhalation and non-wearer fluid drainage periods the cover is disposed over the plurality of apertures to help prevent or reduce escape of the medical gas through the plurality of apertures; wherein during exhalation by the wearer a force of an exhalation breath of the wearer causes to washer to move away with respect to the plurality of apertures to allow carbon dioxide from the exhalation breath to escape out through the plurality of apertures so not to be breathed in by the wearer during inhalation;
wherein at least one inlet acting as a connector and is adapted for receiving and utilizing a metered dose inhaler through an internal passageway within the connector.

21. The medical mask of claim 18 wherein the body is structured and constructed from a material that assist in the reduction of facial skin breakdown.

* * * * *